(12) United States Patent
O'Malley

(10) Patent No.: US 10,111,780 B2
(45) Date of Patent: Oct. 30, 2018

(54) GOGGLE LENS AND FACE GASKET ENGAGEMENT SYSTEM

(71) Applicant: Abominable Labs, LLC, Lake Oswego, OR (US)

(72) Inventor: Vincent O'Malley, Portland, OR (US)

(73) Assignee: Abominable Labs, LLC, Lake Oswego, OR (US)

( * ) Notice: Subject to any disclaimer, the term of this patent is extended or adjusted under 35 U.S.C. 154(b) by 191 days.

(21) Appl. No.: 15/407,267

(22) Filed: Jan. 17, 2017

(65) Prior Publication Data

US 2017/0143546 A1 May 25, 2017

Related U.S. Application Data

(63) Continuation-in-part of application No. PCT/US2016/058330, filed on Oct. 22, 2016.

(60) Provisional application No. 62/280,110, filed on Jan. 18, 2016, provisional application No. 62/245,904, filed on Oct. 23, 2015.

(51) Int. Cl.
*A61F 9/02* (2006.01)

(52) U.S. Cl.
CPC .............. *A61F 9/029* (2013.01); *A61F 9/028* (2013.01)

(58) Field of Classification Search
CPC .. A61F 9/029; A61F 9/028; A61F 9/02; A61F 9/022; A61F 9/025; A61F 9/026; A61F 9/027; A63B 33/002; B63C 11/12; G02C 1/023; G02C 5/146; G02C 5/22; G02C 9/04

USPC ..... 2/435, 452; 351/140, 142, 143, 152, 153
See application file for complete search history.

(56) References Cited

U.S. PATENT DOCUMENTS

| | | | |
|---|---|---|---|
| 4,868,929 A | 9/1989 | Curcio | |
| 4,940,884 A | 7/1990 | Gillery | |
| 4,942,629 A | 7/1990 | Stadlmann | |
| 5,363,153 A * | 11/1994 | Bailiff | G02C 11/00 219/201 |
| 5,459,533 A | 10/1995 | McCooeye et al. | |
| 5,471,036 A | 11/1995 | Sperbeck | |
| 5,617,588 A * | 4/1997 | Canavan | A44B 11/04 2/428 |
| 5,815,235 A | 9/1998 | Runckel | |
| 6,047,410 A | 4/2000 | Dondero | |
| 6,704,944 B2 | 3/2004 | Kawainshi et al. | |
| 6,732,383 B2 | 5/2004 | Cleary et al. | |

(Continued)

*Primary Examiner* — Amy Vanatta
(74) *Attorney, Agent, or Firm* — Howard Russell

(57) ABSTRACT

Goggle lens and face gasket engagement system having a lens member with first and second ends, a plurality of latch members pivotably attached to the lens member, one latch member attached adjacent each end of the lens member, each latch member having at least one recessed detent area, a flexible face gasket member further comprising a plurality of supple nub protrusions, each supple nub protrusion for residing in a corresponding one of the recessed detent areas of the latch members, a plurality of other alignment protrusions and receptacles interfacing between the lens member and face gasket, and a strap member interconnecting the latch members for securing the goggle lens and face gasket engagement system to a user's head. Preferably, the goggle lens and face gasket engagement system further comprises a multi-point contact electrical system for heating the lens to prevent fogging.

11 Claims, 6 Drawing Sheets

(56) References Cited

U.S. PATENT DOCUMENTS

| | | | |
|---|---|---|---|
| 6,948,813 B2* | 9/2005 | Parks | A61F 9/025 2/436 |
| 7,648,234 B2 | 1/2010 | Welchel et al. | |
| 7,810,174 B2 | 10/2010 | Matera | |
| 7,856,673 B2 | 12/2010 | Reed | |
| 8,893,314 B2* | 11/2014 | Chen | A61F 9/025 2/426 |
| 9,301,879 B2 | 4/2016 | McCulloch et al. | |
| 2002/0044331 A1 | 4/2002 | Agrawal et al. | |
| 2002/0157175 A1* | 10/2002 | Dondero | A61F 9/025 2/436 |
| 2003/0101507 A1 | 6/2003 | Cleary et al. | |
| 2005/0193478 A1 | 9/2005 | Hussey | |
| 2007/0033718 A1* | 2/2007 | Lin | A61F 9/026 2/448 |
| 2008/0155736 A1* | 7/2008 | Paulson | A61F 9/025 2/441 |
| 2008/0290081 A1 | 11/2008 | Biddell | |
| 2009/0038059 A1* | 2/2009 | McNeal | A61F 9/025 2/439 |
| 2009/0151057 A1 | 6/2009 | Lebel et al. | |
| 2011/0126345 A1* | 6/2011 | Matsumoto | A61F 9/028 2/435 |
| 2011/0225709 A1 | 9/2011 | Saylor et al. | |
| 2013/0068495 A1 | 3/2013 | Hadi et al. | |
| 2013/0091623 A1 | 4/2013 | McCulloch et al. | |
| 2013/0097855 A1* | 4/2013 | Li | A61F 9/025 29/700 |
| 2013/0104300 A1* | 5/2013 | Park | A61F 9/025 2/439 |
| 2014/0157496 A1* | 6/2014 | Ginther | A61F 9/025 2/439 |
| 2014/0317836 A1 | 10/2014 | McCulloch et al. | |
| 2014/0370311 A1 | 12/2014 | Boulord et al. | |
| 2015/0121610 A1 | 5/2015 | Cornelius et al. | |
| 2016/0331591 A1* | 11/2016 | Kilduff | A61F 9/025 |

* cited by examiner

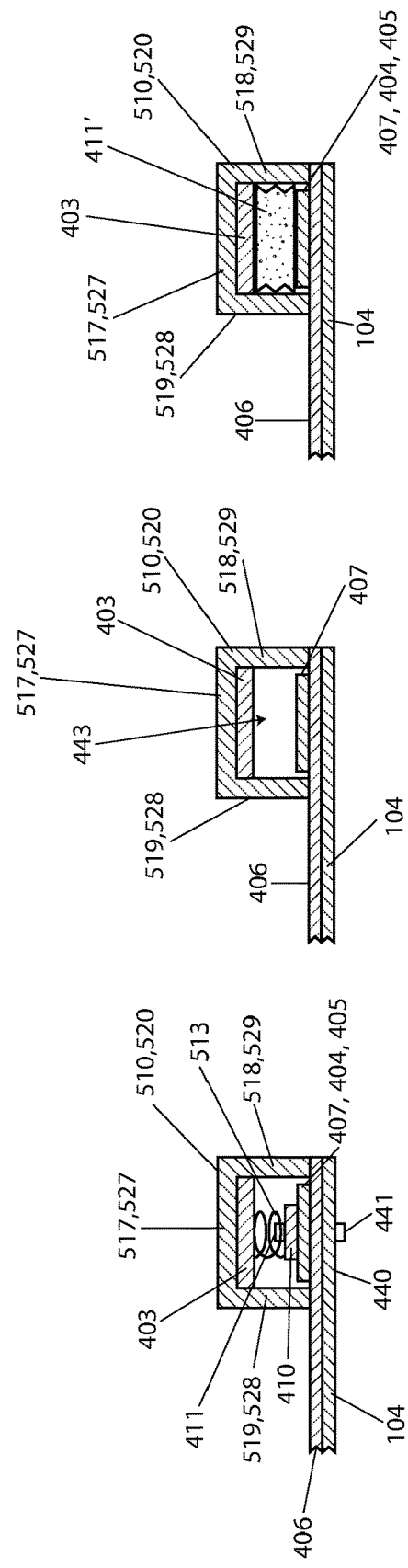

GOGGLE LENS AND FACE GASKET ENGAGEMENT SYSTEM

CROSS-REFERENCE TO RELATED APPLICATIONS

This patent application claims the benefit and priority of U.S. Provisional Patent Application Ser. No. 62/280,110, for Goggle Lens and Face Engagement System, filed 18 Jan. 2016, and is a continuation-in-part application claiming the priority and benefit of PCT Patent Application Serial No. PCT/US2016/058,330, for Electrical Interconnection System for Heating Eye-Shield, filed 22 Oct. 2016, which PCT Patent Application claimed the benefit and priority of U.S. Provisional Patent Application Ser. No. 62/245,904, for Electrical Interconnection System for Customized Heating of an Eye-Shield, filed 23 Oct. 2015.

FIELD OF INVENTION

This invention relates generally to engagement systems for goggles having interchangeable lenses, and more particularly to an engagement system for a readily interchangeable face gasket with a lens that is preferably adapted for interconnection with a battery power source for heating of the lens to prevent fogging.

BACKGROUND OF INVENTION

Sport goggles, such as are often used for skiing, cycling, snow-boarding, motorcycle and ATV riding, paint-balling, standard-issue, ballistics grade, military goggles used for military ground and other operations, or safety goggles used for medical and other scientific purposes, typically have at least comprised a plastic frame or body and a clear plastic, or polycarbonate, see-through lens. Sometimes the plastic body has further been comprised of an anterior body interconnected to a posterior body, the foremost portion of the anterior body being designed for attachment to, carrying and positioning of the lens a comfortable distance from a user's eyes. The posterior body (referred to herein as a face gasket) has comprised a foam rubber, or softer plastic, interface on the most posterior portion of the body for comfortable positioning of the goggle frame body on the user's face around and defining the field of vision for the user's eyes. Such conventional goggles have further comprised an elongated, elastomeric strap attached at either end thereof to corresponding ends of the anterior body, or alternatively to cantilevered, pivoting or non-pivoting, booms, or outriggers, for the purpose of holding the goggles on the head, or helmet, of the user by stretching the strap around the back of the head, or helmet, with the goggle positioned in opposing fashion on the face of the user. It has generally been accepted and understood among goggle wearers that different colors of lenses have been advantageous for different lighting and weather conditions, and further that differently-shaped and various face gaskets would be advantageous for persons having faces of different sizes and shapes.

The earliest conventional goggles did not provide for interchangeable lenses. This resulted in a less useful goggle, as changing lighting conditions through the day have rendered the goggle, with just one lens option, less suitable for distinguishing variations in terrain. In particular, with snowy terrain, it is often difficult to determine the presence of terrain variations because the snow is all one color: white. Different colors, or different darkness, of interchangeable lenses may have facilitated distinguishing variations in such snowy terrain. Further, where the lens of the goggle has become damaged, or broken, such goggles have also required replacement of the entire goggle.

Further, prior art goggles have not so much provided for interchangeable goggle frames (i.e., an inexpensive, throwaway, or interchangeable, frame), except insofar as interchanging a lens on a goggle frame necessarily entails a new goggle frame and lens combination (by virtue of the fact that the lens has changed—not the frame). This has been, at least in part, because there has not been provided in the past a simple interchangeable face gasket for prior art goggles. The lack of interchangeable goggle frames in the prior art may be seen as primarily a function of relative lower cost of prior art interchangeable replacement lenses relative to prior art goggle frames. Thus, the primary emphasis for interchangeability for prior art goggles has opted for a more expensive goggle frame, or body, with a cheaper, more interchangeable, replacement lens, to enable use of the same goggle frame with different lenses in differing lighting and weather conditions, and for lens repairs.

More recently, conventional goggles have allowed for easy replacement of a damaged or broken lens, or replacement of a lens that is no longer suitable for changed lighting conditions. In such goggles, the body has comprised a somewhat flexible, but resilient, molded material forming a relatively deep vertically-oriented groove, often together with a plurality of notches on the lens matched with inflexible pegs in the groove for alignment and retention purposes. The notches and matched pegs have been designed to receive and hold the peripheral edge of the lens in a vertically-oriented fashion in the groove and to retain the lens in proper orientation on the pegs relative to the body.

When a user has desired to remove such a lens, they have pulled the somewhat flexible goggle body members apart, disconnecting the notches and otherwise disassociating the lens from the pegs and groove in the body. Replacement with a different color lens has involved a reverse process of aligning the edge of the lens, and its notches, with their associated groove and pegs, first fitting an upper, or alternatively lower, portion of the lens into its associated groove and pegs, and then fitting the opposite portion of the lens into its associated groove and pegs. This process has been time-consuming and cumbersome, making it difficult for a user to easily interchange lenses, so much so that many have determined to not make an attempt to change the lens in the open, but rather to use a lens that has provided multipurpose, though not ideal, use for most lighting conditions. Alternatively, where users have shown the patience necessary to have repeatedly changed lenses, these goggle bodies have lost some resiliency, have broken, or have cracked, due to repeated stressing of the bodies, and this has led to a lack of effective engagement between the lens and the body.

Responsive to the difficulties of interchanging lenses for these types of goggles, there have been developed goggles having articulated frames designed for opening and closing to allow easier changing to lenses adapted for changed conditions. An example of such a frame is provided by U.S. Pat. No. 5,815,235, to Runckel, for Ski Goggles With Pivotal Frame Members For Interchanging Lenses. Runckel does not provide for interchangeable face gaskets. U.S. Pat. No. 8,800,067 to Saylor et al., for Eyewear With Interchangeable Lens Mechanism, has facilitated the interchanging of lenses of goggles with a biased outrigger, gate or latch pivotably mounted to the goggle frame, for securing the lens relative to the goggle frame, the lens being further held in a proper orientation by one or more engagement members aligned with an aperture, or apertures, in the lens. The outrigger of Saylor is not known to be for the purpose of securing a stretchy strap to the goggle for holding the goggle on a user's head, with or without a helmet. Saylor does not provide for interchangeable face gaskets.

U.S. Pat. No. 6,047,410, to Dondero, for Goggle Frame and Attachment System, provides a goggle frame with a removable hinged strap attachment member attached thereto and adapted for enabling easier clearance of the strap around military, motorcycle or snow sports helmets. The hinged strap attachment member of Dondero is not a latch for directly holding the goggle lens on the frame, or for facilitating interchangeability of the Dondero lens. Dondero does not provide for interchangeable face gaskets.

U.S. Pat. No. 6,732,383, to Cleary et al., for Goggle with Side Arm for Wearing with a Helmet, provides side arms pivotably mounted to the goggle frame thereof for supporting, with a strap, the goggle on a wearer's head, or helmet. Thus, the strap of Cleary et al., is mounted to the pivotable side arms, however, while the arms of Cleary et al. may at best somewhat reinforce the frame of the goggle, to help better retain the lens in the goggle frame, the arms of that device do not comprise a latch for engaging with the lens directly to hold the Cleary et al. lens on the goggle frame. The Cleary et al. goggle does not provide for interchangeable face gaskets.

A goggle provided by Scott Sports, SA, referred to as an LCG goggle, provides a latch mounted on a more traditional goggle frame having an anterior more rigid portion and a posterior more flexible face interface portion, the latch being operable to engage an attachment bracket on the periphery of the back of a goggle lens for holding the lens on the goggle frame. The Scott latch does not interconnect the goggle strap to the goggle body or lens, and the Scott goggle does not provide for interchangeable face gaskets.

Published US Patent Application No. 2009/0151057, to Lebel et al., for Reversible Strap-Mounting Clips for Goggles, provides first and second orientations for helmetless, and helmet, wearing scenarios, respectively, in a goggle that provides electronics for a heated lens or other electronic application. However, the Lebel et al. goggle does not provide a latch for facilitating interchangeable and easily releasable engagement between the Lebel et al. goggle body and lens, and Lebel et al. does not provide for interchangeable face gaskets.

Goggles are known to have become obscured with moisture when temperature and relative humidity conditions inside of the space defined between the goggle body and the user's face and eyes have been such that a dew point has been reached and condensation has formed like a "fog" on the inner surface of the goggle. This typically has happened when a colder inner surface of the goggle lens has come in contact with a now warmer and more humid area enclosed within the goggle body. There are many possible conditions which may lead to fogging of a goggle, since the dew point of the inside of the lens is affected by varying temperature, moisture, pressure and ventilation conditions. One common example of fogging has occurred when a person who has been skiing, cycling, hiking or engaging in other strenuous work or combat-related activity, stops moving as quickly as before, thus reducing the amount of air flow over the surfaces of the goggle such that temperature differentials between the inner surface of the goggle and the now warmed and moist air trapped within the goggle, have caused condensation and fogging of the inner surface of the goggle lens.

Another example of a cause of fogging involves a significant increase in physical exertion and activity which increases the amount of moisture and heat trapped within the goggle. In this scenario, perspiration and a higher incidence of exhaled moist warm air, associated with increased physical exertion, travels into the goggle enclosure. In such a case there has existed a greater imbalance in temperature between the inner surface of the goggle lens and the moist warm air trapped within the goggle, causing condensation and fogging on the inner surface of the lens.

Thus, fogging is a common problem with goggles, and this has occurred in various situations involving temperature extremes, when warmer temperatures caused by perspiration and respiration have entered within the goggle enclosure in a warmer state than relatively colder temperature conditions outside of the goggle body. Of course this problem has ranged from being annoying to the user, to presenting a very dangerous situation where the user's field of vision has been greatly diminished while the user has been traveling at high speeds among fixed obstacles, such as trees, widely varying terrain such as bumps, cliffs, or other participants, or the user has otherwise been unable to clearly see an intended target or an enemy combatant. The problem of fogged goggles has resulted in injury and even death among goggle users.

Responsive to this common, annoying and even dangerous condition, great attention has been paid to solutions to the problem of fogging of goggles. For instance, numerous efforts have been made to increase the amount of passive airflow into the goggle. Examples of such may be found in US Patent Application Serial No. 20050193478 to Hussey, for Goggle Attachment System, and U.S. Pat. No. 6,665,885 to Masumoto, for Goggles. Another example of passive airflow is found in the Julbo Aerospace goggle, by Julbo SA, which entails a lens able to be pulled out away from the lens frame for enhanced airflow to prevent fogging. None of the foregoing described goggles provides for interchangeable face gaskets.

Despite best efforts to produce a goggle that utilizes passive air-flow means for defogging the lens of the goggle, there are often present conditions which have rendered passive air-flow means of de-fogging ineffective—such as excess exertion causing corresponding body heating and excess humidity and temperature conditions within the goggle. Such conditions have overwhelmed the ability of the passive means to overcome the temperature and humidity differentials presented by exertion by a user in cold, icing conditions or accumulation of snow clogging ventilation means. Also, sometimes a user's clothing, especially such as scarves or face masks, have impeded intended airflow of such goggles, rendering them ineffective.

Another known attempt to resolve goggle fogging problems has included double-pane goggle lenses, such as for example may be found in Published US Patent Application No. US2006/0272078, to Polinelli et al., for Apparatus and Methodology to Mitigate Fogging on Dual Lens Sports Goggle. In addition to venting, Polinelli et al. provides a dual-pane lens assembly having a gasket disposed between the outer and inner lens and forming an air tight space to mitigate against fogging. This type of goggle utilizes the air space between the two goggle lenses to insulate, and therefore prevent, the inner surface of the lens from becoming so cold as to react to form condensate thereon when it comes in contact with the warmer and more moist air in the air space between the user's face and the inner surface of the inner goggle lens. While the presence of a dual-pane lens system in a goggle may help prevent some fogging, it has not been entirely adequate to completely prevent fogging, as is evidenced by ongoing and continued efforts attempting to solve the problem of goggle lens fogging with lens coatings, active technologies such as a fan in a goggle, and heated-lens goggle systems.

Dual-lens goggles to minimize fogging have become very common in the marketplace. But these goggles require additional lens material to manufacture, and thus they are more bulky and more expensive to manufacture. Nevertheless, such goggles have persisted in the marketplace because of their fog fighting properties. If it were possible to have a simpler goggle, perhaps even with a single-pane lens, that was also able to be fog-free under virtually all conditions, it may be preferable to users. This result could obtain because of the simplicity of manufacturing a less bulky, single-pane lens system at a relative cost savings.

There have also been provided goggles, each having an interior fan to ventilate the enclosed space between the goggle inner lens and the user's face, to mitigate the conditions leading to fogging. An example of such a system has been provided in U.S. Pat. No. 5,452,480, to Ryden, for Ski Goggles. One problem of such a device is that it does not necessarily overcome icing, snow accumulation or other blockage of outer goggle vents, thus rendering such a system less effective. Also, the Ryden system does not provide for readily-interchangeable face gaskets.

Regardless of the exact causes of fogging of a goggle in a particular situation, it is understood that sufficient heating of the inner surface of the lens of the goggle comprises an effective means of removing fog from the lens and preventing further fogging. Accordingly, there have been developed various means of actively heating the inner surface of the goggle lens. One such means has comprised the placement of wires, or a resistive film surface, on the inner surface of the goggle lens, which wires or resistive surface have been attached to an electrical power source such as a DC battery carried on the goggle headband or jacket of the user in order to provide sufficient power to heat the lens. Examples of such a method of heating the lens of the goggle have been disclosed in U.S. Pat. No. 4,868,929, to Curcio, for Electrically Heated Ski Goggles; U.S. Pat. No. 5,459,533, to McCooeye et al., for Defogging Eye Wear; Published US Patent Application Serial No. US2009/0151057, to Lebel et al., for Reversible Strap-Mounting Clips for Goggles; and Published US Patent Application Serial No. US2013/0091623 A1, to McCulloch et al., for Goggle with Easily Interchangeable Lens that is Adaptable for Heating to Prevent Fogging. None of the foregoing patents or patent applications provide for readily-interchangeable face gaskets.

Thus, prior methods of accomplishing contact between the battery and a lens have been devised such as are described in U.S. Pat. No. 4,868,929, to Curcio, for Electrically Heated Ski Goggles; and U.S. Pat. No. 5,459,533, to McCooeye et al., for Defogging Eye Wear. Curcio discloses a simple, single-point wire contact system between the battery either on the frame or on the belt of a user. A downside of such a system is that the wires are visible, may obstruct vision, and may lead to uneven heating of the entire lens. This inefficiency, in turn, has resulted in wasted energy and corresponding less battery longevity for the system.

McCooeye et al. discloses a heater comprised of a thin layer of chrome, and the contacts are thicker layers of chrome in electrical contact with each other. Of course, the chrome of both the heating element and the bus bars is visible, and this may be undesirable. Further, neither Curcio nor McCooeye provides for readily-interchangeable face gaskets.

Thus, there have been devised various goggle means addressing a desirability for easily interchanging the lens on a sport, a standard-issue military, and/or a medical or a safety goggle, and a desirability for maintaining such a goggle fog free. But there yet exists a need for a sport, standard-issue military, medical or safety goggle that provides a readily-interchangeable face gasket for simple and cost-effective adaptation of the goggle to multiple persons, each having differing facial characteristics, as well as an easily interchangeable lens system, both of which would also preferably be provided with an active, effective means of evenly heating the preferably single-pane lens of such a goggle to prevent fogging. In particular, there exists a need for an efficient and effective means of both releasably attaching the lens of a goggle to its body, and in particular its face gasket, to allow fit for different facial characteristics and different comfort levels and options for sealing the goggle to a user's face. Preferably such a lens and goggle/gasket engagement system may include a simple means for interconnection of the lens to a source for heating of the lens, especially when a less bulky single lens system is employed, such as for example would be advantageous in a tactical goggle, so that the presence of a lens heating system would be especially helpful to prevent fogging. Ideally, such a system would be easy to operate, and would be provided in a goggle that is able to provide even heating to the heated lens in a relatively inexpensive, simple, reliable (defect-free) manufacturing process. Thus, such a goggle would be more affordable and more dependable for sporting, medical, scientific and standard issue military applications.

Electronic components require a moisture-free environment, and moisture needs to be prevented from entering into areas where electronic components and wiring of an electronic device are housed for the device to work reliably over extended periods of time. Access by moisture to electronic components may cause short circuits, it may permanently damage the electronic components, it may corrode electrical components, and it may lead to temporary or total failure of the components and device as well.

In particular, a heretofore unknown problem arises with prevention of water and moisture from entering into goggle electronic components that are adapted for easy interchange of heated lenses, since part of the electronic circuit for such a goggle typically resides on a removable lens, and the other part of the circuit has resided in the goggle body. While a non-interchangeable lens goggle's electronic components may be relatively easily sealed against moisture, a heated-lens goggle adapted for easily interchangeability of the lens presents moisture issues that must be overcome with a novel approach. Thus, interconnecting the two parts, the lens and the body, and detaching the same, in a manner as simply as possible in as few simple steps as possible, has proven challenging to resolve while also providing an installed interconnection that doesn't risk exposure of electronics components of the goggle to moisture and water damage during use of the goggle.

PCT Patent Application Serial No. PCT/US2016/14944, to McCulloch et al., for Goggle With Easily Interchangeable Lens that is Adaptable For Heating to Prevent Fogging, provides an effective system for preventing moisture from entering into the goggle's electronics, but it provides for the electronics and battery for the goggle residing in the goggle body itself. In a goggle involving a smaller profile, such as a tactical goggle with ballistics grade lenses, or a goggle for medical or scientific use, such a smaller body profile prevents retention of a battery of sufficient size to allow heating of the lens for extended periods of time on the goggle body frame itself. Accordingly, a solution for incorporating an external battery into the system with a water-resistant interconnection means is required for such a smaller goggle.

Further, in such a goggle having a smaller profile, there is needed a new and reliable means for integrating the contacts for heating the goggle into a frame member for the lens and for making consistent multi-point contacts with the heating element on the lens for even and consistent heating of the same. As set forth in PCT Patent Application Serial No. PCT/US2016/058,330, to O'Malley et al., for Electrical Interconnection System for Heating Eye-Shield, and U.S. Pat. No. 9,210,737 to Cornelius, for Multiregion Heated Eye Shield, even heating of irregularly-shaped eye-shields has been problematic before the inventions disclosed in those two patent applications.

U.S. Pat. No. 5,471,036 to Sperbeck for Goggle Defogging System with Transparent Indium-Tin-Oxide Heating Layer Disposed on a Lens provides recognition of the problem of uneven heating of a thin-filmed heating element on a goggle lens over the bridge of a user's nose, and other areas, and provides that "the ITO coating includes an interior heating zone (33) that is electrically isolated form the edge of the inside layer." Further, Sperbeck provides, "the region (48) where the bus bars cross the nose area (41) of the goggle lens is isolated from the interior heating zone (33)." Sperbeck further provides: "As a result, the bus bar only contacts the interior heating zone along the top of the goggle lens and along the bottom of the eye regions (37) of the goggle lens located on either side of the nose area (41)." However, Sperbeck does not teach use of a bus bar interconnection system having a channel member or the like specifically for the purpose of allowing partial contact of the bus bar with multi-point contacts at strategic locations for supporting even, or customized, heating of an irregular-shaped eye-shield. Further, Sperbeck does not provide a less-costly-to-manufacture engaging system, wherein a specific heating pattern may be applied to the eye-shield to prevent hot spots or to otherwise provide customized heating. Thus, there is needed a multi-point contact system together with an engagement system for effectively holding the multi-point contact areas of the interconnection system against the bus bar, and while allowing other areas of the heating element to be out of contact with the bus bar.

Rather, the bus bars of Sperbeck make a uniform, smooth-transition path across the path of the lens, and they are not taught to be used in conjunction with a multi-point interconnection system for making electrical contact with only portions of the bus bar. Instead, Sperbeck teaches that "The interior heating zone of the ITO coating can be electrically isolated by scoring a groove around the periphery of the ITO coating. Alternatively, acid etching can be used to remove a peripheral part of the ITO coating." Sperbeck makes use of a tab 43 and connector 46 for interconnecting the bus bar, leads from the battery, and the ITO on the eye-shield substrate.

In U.S. patent application Ser. No. 14/040,683, for Multiregion Heated Eye Shield, to Cornelius, there is provided an anti-fog eye-shield having an apportioned thin resistive-film heater on the eye-shield to enable even heating of the lens, or other custom heating of the lens, for use in an anti-fog goggle, an anti-fog dive mask or other portable transparent anti-fog eye-protecting shield. In that application, there is taught apportioning of the heater on the eye-shield with either a split bus bar for each apportioned heating area, or a single bus bar for multiple apportioned heating areas. Cornelius does not teach an altered-structure, or altered-configuration, multi-point contact interconnection system for holding only multi-point contact portions of the goggle interconnection contact system against the bus bar, while allowing other portions of the bus bar, and/or the heating element, to be out of contact with the multi-point contact interconnection system. Such a system would allow for strategically-located application of power to the bus bar to prevent hot spots, or to otherwise provide customized heating.

Accordingly, there is also needed in a goggle with a lens and readily-interchangeable face gasket engagement system, a means of effectively securing consistent, reliable and durable electrical contact between the heating element of the goggle system and the battery power source for the goggle system.

SUMMARY OF THE INVENTION

In accordance with a first aspect and embodiment of the invention, there is provided a goggle having a lens and interchangeable face gasket engagement system comprising: a lens member having a posterior inner surface and first and second ends and latch members pivotably attached to the lens member, one latch member attached adjacent each end of the lens member, each latch member having at least one face gasket member engagement portion. Further, there is provided a flexible face gasket member comprising a plurality of corresponding latch member engagement portions, each latch member engagement portion of the gasket member for engaging a corresponding one of the gasket member engagement portions of the latch members. At least one of the lens member and the flexible face gasket member further comprises a plurality of other alignment protrusions thereon, whereas the other of the lens member and the flexible face gasket member further comprises corresponding receptacles aligned with the other protrusions, for aligning and helping to retain the face gasket member with the lens member when engaged thereon. Still further, there is provided a strap member having first and second ends, each end interconnected to one of the latch members for securing the goggle lens and face gasket engagement system to a user's head.

Preferably, in accordance with this first aspect of the invention, the lens member of the goggle is further provided having an anterior outer surface, an upper peripheral portion and a lower peripheral portion. Further, preferably, each face gasket member engagement portion of each latch member, pivotably attached to both the upper peripheral portion and the lower peripheral portion of the lens member adjacent each of the first and second ends of the lens member, comprises a recessed detent area. Still further, preferably, each latch engagement member portion of the flexible face gasket member comprises a supple nub protrusion for residing in the recessed detent area of the latch member.

Preferably, in accordance with this aspect of the invention, the latch member pivots on co-linear pivot points, or posts inserted permanently, or removeably, on the upper and lower peripheral portions of the lens member, or alternatively to frame members edging, or enveloping, the circumference peripheral edges of the lens member. Thus, in accordance with this preferable embodiment of this aspect of the invention, each latch member pivots to engage and disengage the latch member with the supple nub protrusion characterized by deformation of the supple nub protrusion at a first instance of initial pivoting engagement of the latch with the supple nub protrusion, followed by further deformation of the supple nub protrusion during continued partial pivoting engagement of the latch with the supple nub protrusion, followed by a resilient return of the supple nub protrusion to its original shape fitting within the recessed area of the latch once the latch is fully pivoted into position for retaining the face gasket. The aforementioned relative engagement process is further characterized preferably by a positive snap, pop, or click, of the supple nub into the recessed area, thus affirming retention of the face gasket by the latch on the lens member.

Preferably, in accordance with this aspect of the invention, there are a plurality of latches so employed, at least one pivotally engaged using collinear pivot points, or posts, as above-described, adjacent each of the upper and lower peripheral portions adjacent each of the first and second ends of the lens member or lens framing members.

Further, preferably, in accordance with this aspect of the invention, the face gasket member comprises upper and lower curved portions and left and right side curved portions formed, as with a unitary member injection molding process, to form a face gasket for interfacing with a user's face per standard goggle interface configuration. Thus the face gasket member preferably comprises a single member comprising four outer corners (upper and lower corners on each the left and right side of the face gasket). These four corners of the face gasket correspond with each pivot point, or post, location of the aforementioned latches at their junction areas, or corners, between the upper and lower peripheral portions of the lens member and the first and second ends of the lens member.

In accordance with this aspect of the invention, the face gasket further comprises a plurality of supple nub protrusions, or preferably a plurality of recessed portions, each leaving a supple nub protrusion portion, one supple nub protrusion corresponding to each latch member recessed area located adjacent a pivot location, and preferably two supple nub protrusions per latch member. Each supple nub protrusion is thus located at upper and lower corners of the face gasket corresponding to each recessed area (both upper and lower recessed areas) of each latch.

Of course it will be appreciated by those of skill in the art that other methods of engaging an interchangeable face gasket with a lens member may be employed without departing from the scope of the invention as claimed. These may include such as a spring and ball combination seating in a detent upon engagement of the lens and face gasket, a flexing hook and recessed area, or other latch and detent system, without departing from the invention as claimed.

Thus, according to this aspect of the invention, a method of installing the face gasket on the lens is provided comprising the following steps: aligning the face gasket with the other protrusions and the corresponding receptacles of the face gasket. This is followed by operating and pivotally moving each of the latch members posteriorly from their open positions towards closed positions, pivotally attached and located at corresponding ends of the lens member, to initially deform corresponding supple nub protrusions upon initial pivoting engagement of the latches with the face gasket. This process proceeds as each latch member continues to deform its corresponding supple nub protrusions upon continued pivoting movement latching engagement of the latch by the user with the face gasket. As the user continues to move the latch to finally fully engage each of the latches' corresponding supple nub protrusions, the supple nub protrusions rebound into a non-deformation state residing within upper and lower recessed areas of the latch in order to retain the lens and the face gasket in a fully-engaged relationship.

In accordance with this aspect of the invention, a further process is provided in which the lens member and the face gasket are disengaged in the reverse order of steps as described above for engagement. That is, to disengage the latch member from one or more corresponding supple nub protrusions on the face gasket, a user simply pivots the latch from its closed position toward an open position, with the latch moving pivotally forwardly, or anteriorly, relative to the most anterior front surface of the lens member, to initially begin to deform the corresponding supple nub protrusions in the reverse, unlatching, pivoting direction. The process continues as the latch is further urged by the user forwardly to continue to deform the supple nub protrusion during continued removal of the latch to disengage the face gasket. The latch is then fully disengaged from the supple nub protrusions, whereupon the supple nub protrusions resiliently return to their original configuration, and the face gasket is fully disengaged from the lens member and its latch or latches.

Preferably, in accordance with this aspect of the invention, the other protrusions extend more rigidly from a posterior surface of the lens member, while the corresponding receptacles are formed into a mating anterior surface of the more flexible face gasket material. However, it will be appreciated by those of ordinary skill in the art that this construction may be reversed with more supple other protrusions extending from the face gasket to engage with other receptacles, or recessed areas, of the lens member to align and help retain these two components in an interchangeably engaged relationship.

This aspect of the invention addresses the need in the marketplace for an readily-interchangeable face gasket that is relatively inexpensive and easy to manufacture and which may be easily designed to conform to users having different facial characteristics and features such as may be the case for different ethnicities or genders of users. Further, this aspect of the invention provides a structure that may be implemented in conjunction with either a spherical or a cylindrical-type lens member, as well as with lens members having different optical, tinting, heating, single-pane/dual-pane, or other electronic capability characteristics. This, in turn, provides an ability of a military, or other team, to have a stock of outer lens members for general use, if desired, while issuing a custom fit face gasket to each member of the team for personalized and more sanitary use.

In accordance with another aspect of the invention, the goggle further comprises a battery retained in a sealed housing on or within the goggle, on the goggle strap member, within the goggle strap member, or at a different location externally of the goggle body or strap. The sealed housing for the battery preferably has an on/off switch thereon. In accordance with this aspect of the invention, the lens member of the goggle is provided with a resistive heating element thereon, such as would be available with a thin-film heater, resistive wires, or other heating element type deposited on the lens using sputtering or other known heating element application technology. Such a heater may be comprised of indium-tin oxide, resistive carbon nanowire technology, or other known heating element material without departing from the scope and spirit of this aspect of the invention. Preferably the heating element is activated when a user depresses the on/off switch to allow the battery to heat the heating element via circuit wires interconnecting the battery and a plurality of bus bars, preferably upper and lower bus bars, painted, as with silver ink, or otherwise deposited or attached, on the heating element on the lens member.

In accordance with this aspect of the invention, the heating element on the lens is preferably releasably interconnected via a combination plug member preferably comprised of a female socket formed on an end of the lens member, the female socket being in electrical contact with the heating element. The combination plug member preferably further comprises a male plug at the end of a wire that is connected with an external battery pack carried in a sealed, waterproof container in, or on, the strap of the goggle. The wire extends through the strap to the male plug member, and the male plug member is able to be easily interconnected with the female socket prior to, or after, engagement of the face gasket with the lens member.

Preferably in accordance with this aspect of the invention, the male portion of the plug member has a conventional seal around it that mates with a correspondingly sealed receptacle on the female socket to prevent moisture from entering into the electronic system of the goggle. It will be appreciated that the male end of the plug may alternatively be located on the lens member, with the female portion of the plug in such case being located on the circuit wire leading from the battery without departing from the true scope and spirit of the invention as claimed.

In accordance with this aspect of the invention, where the upper and lower bus bars are painted on the peripheral upper and lower portions of the heating element on the lens member, contact is made between each bus bar, the heating element and the lens member by means of a contact member on the bus bar further comprising a rivet extending through the contact member, the bus bar, the heating element and the lens member enabling heating the heating element to prevent fogging of the lens member.

Further, in accordance with an embodiment of another aspect of the invention for creating and assuring quality contact(s) between the heating element on the lens and the battery driving heating of the lens, there is provided a multi-point electrical contact system comprising: at least one heating element on the lens, at least one bus bar for contacting the heating element on the lens, at least one, preferably "U"-shaped in cross-section, plastic, or other non-conductive material, channel member that is snapped-on, glued, or otherwise attached, with the open end of the "U" of the channel positioned over the bus bar on the posterior peripheral surface of the lens. Each channel member has located within its channel at least one strategically-located and compressible contact point, the contact point being interconnected with any other contact points and between the heating element and the battery through wiring contained either within, or without, the channel member, or channel members, in a way that the wiring will not come in contact with a bus bar except at the aforementioned contact point(s).

Preferably this aspect of the invention comprises a plurality of "U"-shaped in cross-section channel members, at least one upper "U"-shaped channel member and one lower "U"-shaped channel member, each such channel member being adapted for being snapped-on, glued, or otherwise attached, with the open end of the "U" of each channel member positioned over a bus bar on the posterior peripheral surface area of the lens. Such a channel member has located within its channel (or a recessed area of an "L"-shaped member would suffice) a plurality of strategically-located and compressible contact points, the contact points being interconnected within the channel members with wiring, or other type of conductive strip as described above, between the multi-point contact members and between these and the heating element and the battery through such wiring, or conductive strip, that is retained preferably within the channel members.

It will be appreciated by those skilled in the art that a "U"-shaped channel is not the only way to provide the multi-point system of the invention, but rather any device which provides a sufficient recess to provide that the wiring would not contact the bus bar in some places, but also providing a structure to allow installation of a contact member retained in the channel member for interconnecting each bus bar with the heating element by contacting bus bar with the heating element in desired locations. While preferably this is accomplished with a "U"-shaped channel member enveloping the periphery of the lens member, or a portion of the periphery of the lens member extending over bus bars painted over peripheral portions of the heating element, other shapes of channel members would suffice, such as would be the case with an "L"-shaped member (in cross-section), or a semi-circular member (in cross-section), which may be employed without departing from the true scope of the invention as ultimately claimed.

Still further, in accordance with another embodiment of this aspect of the invention, each bus bar is provided as being retained in the channel member for interconnecting each said bus bar with the heating element, each channel member also retaining at least one contact member for interconnecting each bus bar with the battery via circuit wiring for heating the heating element to prevent fogging of the lens member.

In this embodiment of this aspect of the invention, the bus bars are not painted on the lens member, but rather they are as strips of metallic material retained in the structure of the channel member with contacts built into the channel member at appropriate locations for allowing contact of the bus bar with the heating element at appropriate locations along the periphery of the lens member.

Thus, in accordance with an embodiment of this aspect of the invention, there is provided a goggle having a lens and interchangeable face gasket engagement system and a multi-point contact electrical contact system adapted for connection with a battery for heating the goggle lens comprising: a lens member having a posterior inner surface and first and second ends and latch members pivotably attached to the lens member, one latch member attached adjacent each end of the lens member, each latch member having at least one recessed detent area. Further, in this embodiment of the invention there is provided a flexible face gasket member further comprising a plurality of corresponding supple nub protrusions, each supple nub protrusion for residing in a corresponding one of the recessed detent areas of the latch members, at least one of the lens member and the flexible face gasket member further comprising a plurality of other alignment protrusions thereon, whereas the other of the lens member and the flexible face gasket member further comprises corresponding receptacles aligned with the other protrusions for aligning and helping to retain the face gasket member with the lens member when engaged thereon. This embodiment of the invention comprises a strap member having first and second ends, each end interconnected to one of the latch members for securing the goggle to a user's head, and a battery retained on the strap member, the battery being retained in a sealed housing having an on/off button switch thereon. There is further provided a resistive heating element deposited on a posterior surface of the lens member, upper and lower bus bars for contacting the heating element on the lens member, and upper and lower "U"-shaped cross-section non-conductive channel members attached with an open end of each "U" of each the channel member positioned over each the bus bar. There are further provided a plurality of strategically-located and compressible contact points, the contact points adapted for interconnecting the heating element and the battery via wiring contained partially within the channel members and in a way that the wiring does not contact any the bus bar except at the contact locations within the channel members. Thus, the battery is adapted for heating the heating element on the lens member preferably upon activation by a user pressing the on/off button.

Preferably, in the case where a battery for heating the goggle resides in the strap of the goggle, the wiring of this aspect of the invention interconnecting the multi-point contact points retained within the channel members is partially contained within each channel member and partially contained within the strap of the goggle, the wiring being releasably interconnectable via plug and socket members sealingly joinable at either end of the lens member. The on/off button for turning on and off heating to the lens is preferably located on the battery's waterproof container on the strap, or on the lens frame of the goggle itself.

Further, in accordance with this aspect of the invention, preferably the plug and socket members are partially housed within and behind the latch on whichever side of the goggle the plug and socket members are located, in order to protect them from being dislodged during strenuous activity.

The channel members of this aspect of the invention may be formed to the contour of the lens member inner (posterior) surface, whether cylindrical, spherical, flat, or otherwise, and they may be adapted for being interconnected with the lens underneath a plastic lens frame, or behind a mirrored or dark lens, in order to hide the channel members from external view.

In accordance with another embodiment of this aspect of the invention, there is provided an alternative embodiment contact member comprising a channel member having interconnected multi-point contacts comprised of a compressible, spongy, conductive material for making contact with the interconnecting wire, path, or conductive strip within each channel member.

In accordance with this aspect of the invention, preferably the multi-point contact members are strategically located along an electrical wire, path, or other conductive strip, housed within the channel member, the contact points being adapted for contacting the bus bar at strategic locations along each bus bar, or multiple split bus bars, to account for even heating of the lens resulting from an irregular shape and size of the lens and/or resistive losses along the bus bar lengths. Thus the bus bar is also preferably broken over the bridge of the nose area of the lens member to aid in preventing a hot spot over the bridge of the nose that would otherwise result. In these ways, consistent and even heating of the lens is aided.

Further, as with the previous aspect of the invention, this aspect of the invention also preferably comprises as sealed plug for interconnecting wiring from the battery, if carried on the strap, with the lens member, in order to provide a releasable connection between the battery and the heating element on the lens member.

These latter heated lens aspects of the invention allow for an active, battery-powered, heating technology to be readily applied in accordance with a less expensive and less time-consuming manufacturing process, in order to provide a robust interconnection for power to the heat the lens in order to prevent fogging of the lens.

BRIEF DESCRIPTION OF THE DRAWINGS

FIG. 5B is a detailed cross-section view showing a contact point and interconnection wire located at multiple locations in the channel members as illustrated in FIG. 5A;

FIG. 5C is a detailed cross-section view showing a location along the upper channel member located as shown in FIG. 5A and where no contact point is present; and FIG. 6 is a detailed cross-section view showing an alternate embodiment cross section of a contact point able to be used in channel members like those shown in FIG. 5A.

DETAILED DESCRIPTION

Figure 1:
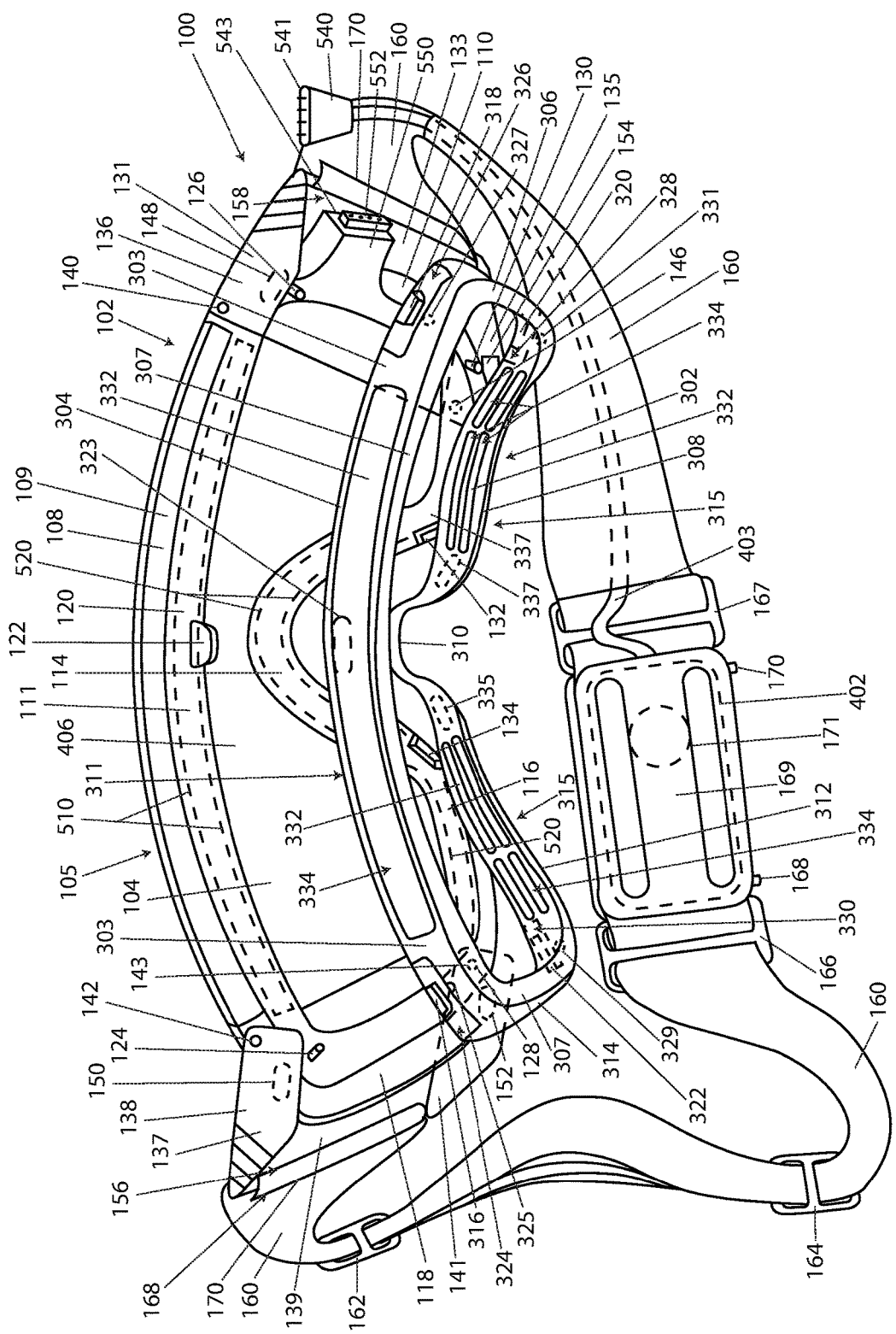
FIG. 1 is a rear perspective view of an anti-fog goggle having an interchangeable goggle lens and face gasket engagement system, shown with the lens and the face gasket apart to illustrate the features of the engagement system, and in accordance with an aspect of the invention.
Figure 2:
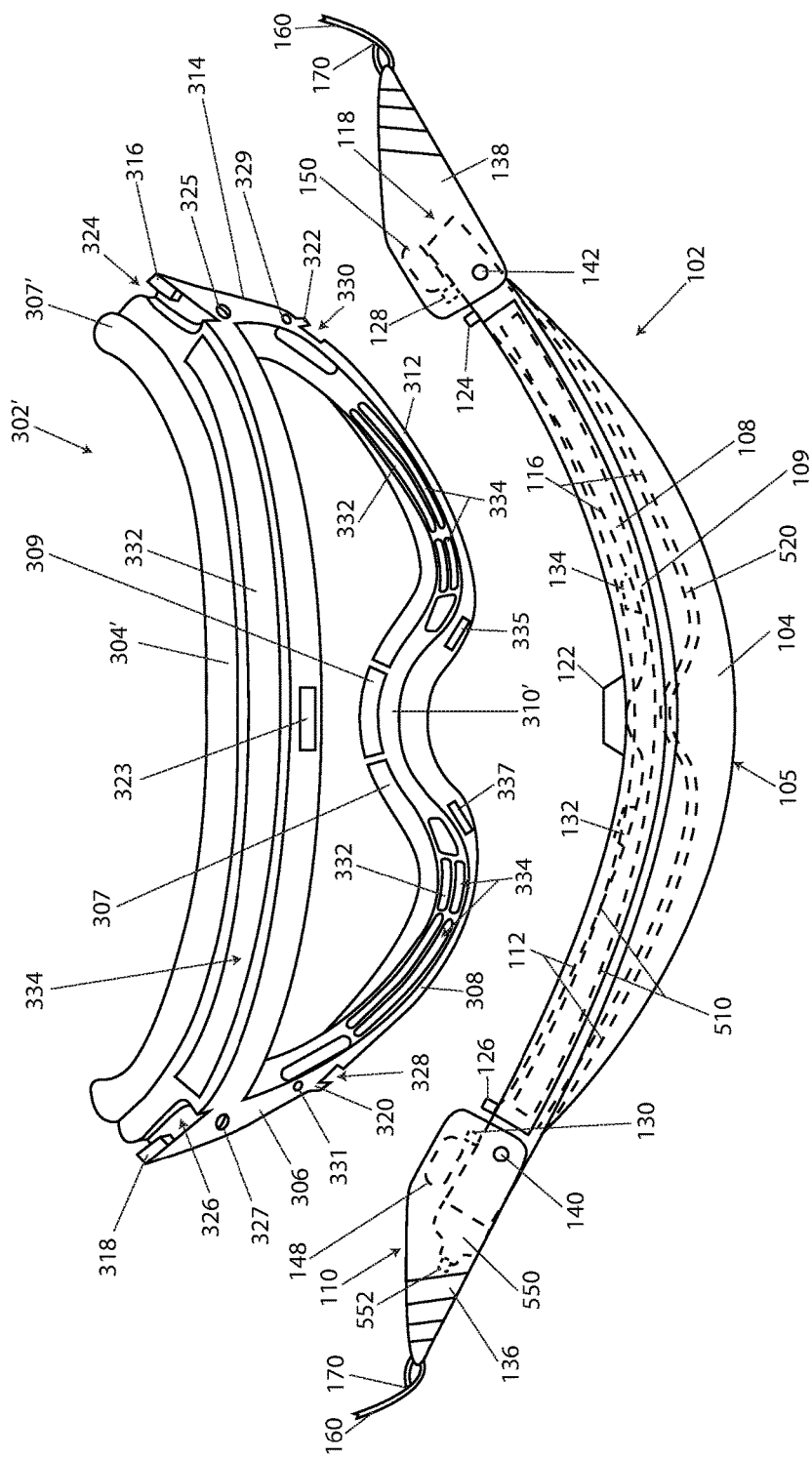
FIG. 2 is a top front perspective view of an alternate interchangeable face gasket having a narrower face interface member and that mates with the same lens member (shown in FIG. 2) as shown in FIG. 1.

Referring to FIGS. 1 and 2, there is shown a goggle with lens and face gasket engagement system 100 comprising a lens member/lens frame member 102 and a face gasket member 302. The lens member/lens frame member 102 is preferably comprised of a polycarbonate lens which may be injection molded as a single lens. It will be appreciated, however, that a dual lens construct, as is known in the art, may be implemented with the invention without departing from the true scope and spirit of the invention as set forth in claims based upon this specification. The lens member 102 may further preferably comprise a plurality of frame members made of a relatively rigid plastic, further comprising a top frame member 108, a right side frame member 110 (from the perspective of a wearer), a bottom right side frame member 112, a nose bridge frame member 114, a bottom left side frame member 116, and a left side frame member 118, which are engaged with the lens member 102 around a posterior periphery of the lens member. The frame members 108, 110, 112, 114, 116, 118 may be suitably injection molded as a unitary frame member and attached to the lens member as is known in the art.

The top frame member 108 comprises an upper surface 109, a posterior surface 111 and left and right ends at which the top frame members joins with each of the side frame members 110, 118. Likewise the two bottom frame members 112, 116 form a unitary underframe portion together with the nose bridge frame member 114. The two bottom frame members 112, 116, the nose bridge frame member 114, the two side frame members 110, 118, and the top frame member 108, together preferably all form a unitary frame member adjacent the posterior periphery of the lens member 102.

In the embodiment of the invention shown in the Figures and the Appendix materials, designated as Appendix A, the lens is an "infinity"-type lens in that it covers the anterior surface of each of the aforementioned frame members 108, 110, 112, 114, 116, 118.

At junction areas of each of the frame members 108, 110, 112, 114, 116, 118, there are a plurality of alignment and retention other protrusions 124, 126, 128, 130, and alignment and retention teeth 122, 132, 134. These alignment and retention other protrusions 124, 126, 128, 130, and teeth 122, 132, 134 are preferably integrally molded with the frame members 108, 110, 112, 114, 116, 118 during their construction and are found on a posterior surface 111 formed by the frame members. The alignment and retention other protrusions 124, 126, 128, 130 and teeth 122, 132, 134 serve to align an interchangeable face gasket 302 as further described below.

At junction areas of each of the frame members 108, 110, 112, 116, 118 (not the nose bridge frame member), there are located a plurality of collinear pivot pin pairs 140, 146 and 142, 143. Collinear pivot pin pair 140, 146 is located near upper and lower right junction areas between frame members 108, 110, 112, and collinear pivot pin pair 142, 143 are located near upper and lower left junction areas between and attached to frame members 108, 118, 116. The collinear pivot pin pairs 140, 146, 142, 143 serve as pivot hinges. The pivot pin pairs, or posts, pivotably attach a pair of corresponding latch members 136, 138 to the frame members, such that the latch members are free to pivot through vertical planes between open, closed and intermediate positions, about the collinear pivot pin pairs at each end of the lens member 102 and associated frame members 108, 110, 112, 114, 116, 118. Latch member 136 is shown in a closed position, and latch member 138 is shown in an open, or intermediate, position in FIGS. 1 and 2. However, because the face gasket members 302 (FIG. 1) and 302' (FIG. 2) are shown separated from the lens member 102, the latch members 136, 138 are not engaged with the face gasket members, but fully engaged lens and face gasket members with latches in closed position are shown in Appendix A.

The latch member 136 is preferably comprised of a central member 133, that is either slightly curved, or alternatively planar, with preferably integrally injection molded upper and lower perpendicular wall members 131, 135. Likewise, the latch member 138 is preferably comprised of a central member 139, that is either slightly curved, or alternatively planar, with preferably integrally injection molded upper and lower perpendicular wall members 137, 141.

At outermost ends of the latch members 136, 138, there are included slots 158, 168, respectively, in which ends of a strap 160 are preferably threaded and either sown at 170, or otherwise retained in the slots, for holding the goggle with lens and face gasket engagement system 100 on a user's face and head, or helmet being worn by the user. In addition to their pivoting, latching and engaging functions described further hereafter, and while it will be appreciated that other shapes of latch members may be used without departing from the true scope and spirit of the invention as claimed, the latch members 136, 138 serve several other useful functions. One function the latches 136, 138 serve is to provide a cantilevered, flared attachment point for the strap 160 so that it is more readily worn with a helmet without pulling on the user's face. Another function the latches 136, 138 serve is to cup each end of the lens 102 so as to prevent debris, wind, snow, etc. from impacting the user at that location. Further, as shown, latch 136 serves to protect a plug-in connection point 540, 550, described further hereafter, from impact, jarring, or elements, such as water intrusion during use in adverse weather conditions.

Each latch member 136, 138 further preferably comprises a pair of recessed detent areas 148, 154 and 150, 152, respectively, for engaging with portions of the face gasket 302 as described further hereafter.

Referring now specifically to FIG. 1, a readily-interchangeable face gasket member 302 is provided. Face gasket 302 is preferably comprised of a unitary, injection molded, ring of plastic Thermoplastic Polyurethane (TPU) material preferably generally in the shape of the periphery of the lens member 102. The face gasket 302 has an upper brow portion 304, and the following other integral curvilinear portions: a right side portion 306, a right side lower portion 308, a nose bridge portion 310, a left side lower portion 312, and a left side portion 314. As is common in the art, each of the aforementioned portions 304, 306, 308, 310, 312, 314 of the face gasket 302 is designed to contact and interface the goggle with lens and face gasket engagement system 100 with the user's face adjacent the face gasket during wear, thus making a seal around the eyes of the user and over the bridge of the nose of the user during wear.

On an upper surface of, and at the corner, or junction, of upper brow portion 304 and right side portion 306 of face gasket 302, there is provided an upper right recessed area 326 defining an upper right supple nub protrusion, or detent, portion 318 for engaging with recessed area 148 of latch 136 as further described herein. On the upper surface of, and at the corner, or junction, of upper brow portion 304 and left side portion 314 of face gasket 302, there is provided an upper left recessed area 324 defining an upper left supple nub protrusion, or detent, portion 316 for engaging with recessed area 150 of latch 138 as further described herein.

On a lower under surface of, and at the corner, or junction, of right side lower portion 308 and right side portion 306 of face gasket 302, there is provided a lower right recessed area 328 defining a lower right supple nub protrusion, or detent, portion 320 for engaging with recessed area 154 of latch 136 as further described herein. The lower right recessed area 328 and the lower right supple nub protrusion portion 320 face in an opposing direction on face gasket 302 than the upper right recessed area 326 and upper right supple nub protrusion portion 318, since the upper right recessed area and upper right supple nub protrusion is on an upper surface 303 of the upper brow portion 304 of the face gasket 302 and the lower right recessed area 328 and supple nub protrusion 320 are on a lower surface 315 of the right side lower portion of the face gasket 302. In other words, the upper and lower supple nub protrusions 318, 320, respectively, face in opposing directions and are aligned with their respective latch recessed areas 148, 154.

On a lower under surface of, and at the corner, or junction, of left side lower portion 312 and left side portion 314 of face gasket 302, there is provided a lower left recessed area 330 defining a lower left supple nub protrusion, or detent, portion 322 for engaging with recessed area 152 of latch 138 as further described herein. The lower left recessed area 330 and the lower right supple nub protrusion portion 322 face in the opposite direction of the upper left recessed area 324 and upper left supple nub protrusion portion 316, since the upper left recessed area and upper left supple nub protrusion is on the upper surface 303 of the upper brow portion 304 of the face gasket 302 and the lower left recessed area 330 and lower left supple nub protrusion 322 are on lower surface 315 of the left side lower portion of the face gasket 302. In other words, the upper and lower supple nub protrusions 316, 322, respectively, face in opposing directions and are aligned with their respective latch recessed areas 150, 152.

The face gasket 302 is comprised of a softer, more flexible material than the lens member 102, such as may be effectively comprised of Thermoplastic Polyurethane (TPU). This allows the face gasket 302 to conform to a user's face. The face gasket 302 may alternatively be processed on extrusion as well as injection, blow and compression molding machines as may be desirable.

An anterior surface 311 of the face gasket 302 further comprises definition of a plurality of protrusion receptacles, or holes, 325, 327, 329, 331 corresponding with and adapted for receiving and releasably retaining the alignment and retention other protrusions 124, 126, 128, 130 of the lens member 102, respectively. Further, the anterior surface 311 of face gasket 302 comprises a plurality of teeth receptacles, or rectangular holes, 323, 331, 335 corresponding with and adapted for receiving and releasably retaining the alignment and retention teeth 122, 132, 134 of the lens member 102, respectively. These alignment and retention members and teeth, and corresponding receptacles, are used for aligning and assisting with engagement of the anterior surface 311 of the face gasket 302 on a mating posterior surface 111 of the lens frame members 102.

Figure 3:
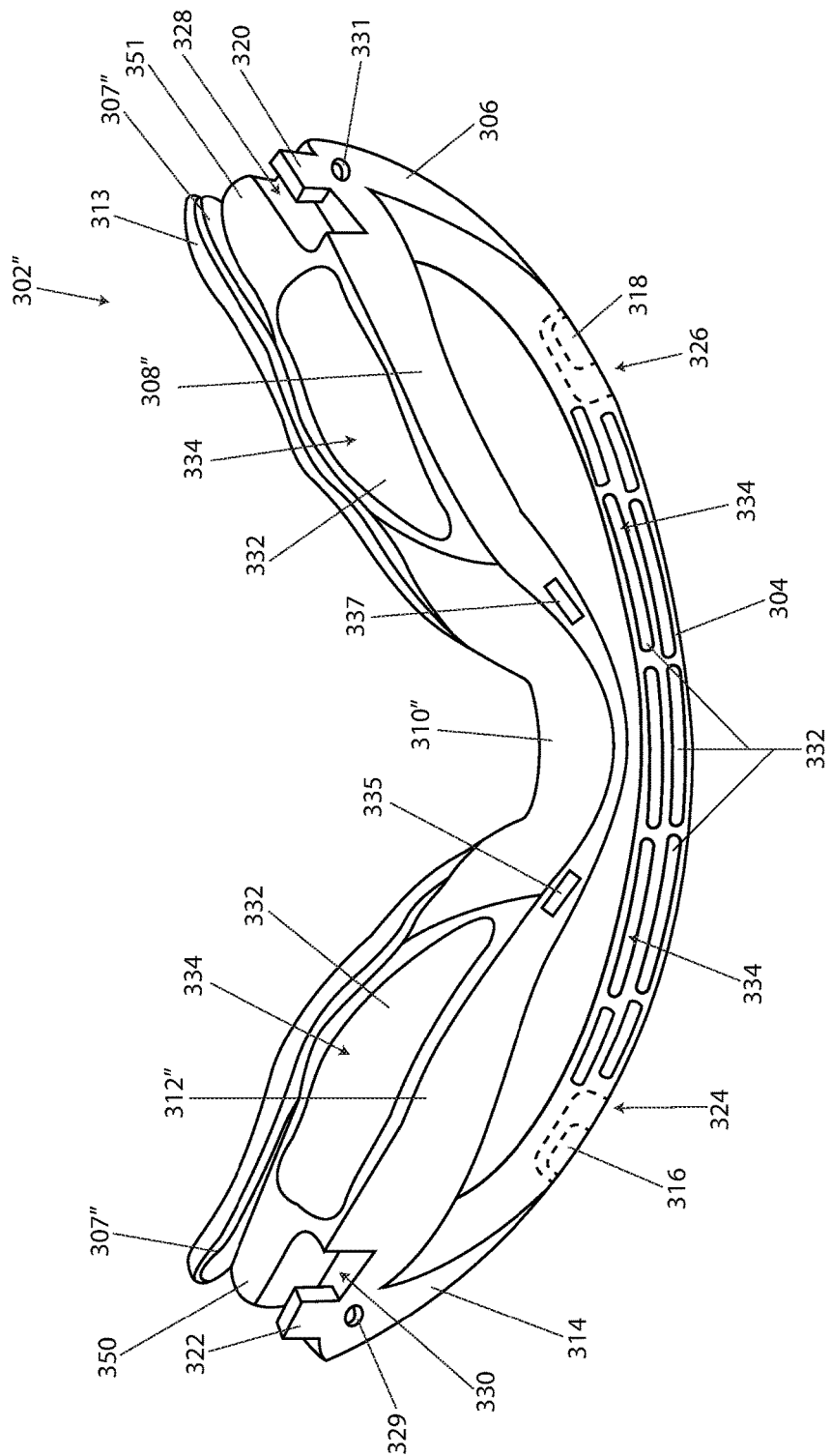
FIG. 3 is a bottom perspective view of an alternate interchangeable face gasket that has a wider and less deep nose well and that would mate with the lens member of the goggle of FIG. 1.

The posterior surface 307 of face gasket 302 is thin and more wide to accommodate a user with larger facial features. Also, alternatively, the posterior surface 307 may include an additional layer of felt, or other soft material, 313, as shown at 307" in FIG. 3, to provide for greater comfort of a user. Still further, as shown in FIG. 3, thicker materials at the lower portions of the face gasket 308", 310", 312" may be incorporated so as to accommodate users having smaller facial features in those areas. Also, as shown in FIG. 3, a flatter nose bridge portion 310" may be used so as to better accommodate users having that type of facial feature.

Each of the face gaskets of FIGS. 1-3 are provided with upper and lower vents 334 and foam, or fabric, covering 332, to allow passage of air for ventilation while keeping debris from entering into the goggle enclosure.

It will be appreciated by those of skill in the art that other methods of engaging an interchangeable face gasket with a lens member may be employed without departing from the scope of the invention as claimed. These may include such as a spring and ball combination seating in a detent upon engagement of the lens and face gasket, a flexing hook and recessed area, or other latch and detent system, without departing from the invention as claimed.

A method of installing the face gasket 302 on the lens 102 is provided comprising the following steps: Aligning the face gasket 302 receptacles 325, 327, 329, 331, 323, 335, 337 with the corresponding other protrusions 124, 126, 128, 130 and teeth 122, 134, 132 of the lens member 102 and engaging the other protrusions and teeth in their corresponding receptacles of the face gasket. Operating each of the latch members 136, 138 posteriorly from an open position (e.g., latch member 138 is shown open, and latch 136 is shown closed) towards a closed position, both positions located pivotally at each corresponding end of the lens member 102, to initially deform anterior edges of the latches corresponding supple nub protrusions 318, 320 and 316, 322, respectively, upon initial pivoting engagement of the latch with the face gasket. This process of operation towards installation is continued to continue to mostly deform each of the corresponding supple nub protrusions 318, 320 and 316, 322, respectively, with and upon continued pivoting movement latching engagement of the corresponding latches 136, 138 with the face gasket 302. Finally, at the full extent of travel to closure of each latch 136, 138, the latches finally fully engage with their corresponding supple nub protrusions 318, 320 and 316, 322, respectively. Thus, the supple nub protrusions 318, 320 and 316, 322 rebound with a "pop" sound into a non-deformation state residing within upper and lower recessed areas 148, 154 and 150, 152, respectively, of the latches to retain the lens 102 and the face gasket 302 in a fully-engaged relationship. The "pop" sound lets the user know that the face gasket 302 is properly seated and engaged.

Further, there is provided a process for disengaging the face gasket 302 and the lens 102 using the reverse order of steps as described above for engagement of these two components. To disengage each latch member 136, 138 from their corresponding supple nub protrusions 318, 320 and 316, 322, respectively, a user simply pivots the latches from their closed positions towards open positions, with the latches moving pivotally forwardly, or anteriorly, relative to a most anterior front surface 105 of the lens member 102, to initially begin to deform posterior edges of the supple nub protrusions in the reverse, unlatching, pivoting direction, to continue to deform the supple nub protrusions during continued removal of the latches to disengage the face gasket 302 from the lens member 102, and to fully disengage the latches from the supple nub protrusions. Thereafter, the supple nub protrusions 318, 320 and 316, 322 resiliently return to their original configuration, and the face gasket 302 may be fully disengaged from the lens member 102 by pulling apart the other protrusions 124, 126, 130, 128 and teeth 122, 132, 134 from their respective receptacles 325, 326, 331, 329 and 323, 331, 335 to separate the two components.

Preferably, in accordance with this aspect of the invention, the other protrusions 124, 126, 130, 128 and teeth 122, 132, 134 extend more rigidly from posterior surface 111 of the lens member 102, while the corresponding receptacles are formed into a mating anterior surface 311 of the more flexible face gasket 302 material. However, it will be appreciated by those of ordinary skill in the art that this construction may be reversed with likely, though not necessarily, more supple other protrusions extending from the face gasket to engage with other receptacles, or recessed areas, of the lens member to align and help retain these two components in an interchangeably engaged relationship without departing from the true spirit of the invention as claimed.

Referring now specifically to FIG. 2, an alternative face gasket 302' is disclosed. Face gasket 302' is very similar in all respects to face gasket 302, except that face gasket 302' includes a larger and narrower posterior face interface area 307' so as to be adapted for persons having smaller and narrower facial features.

Referring now specifically to FIG. 3, another alternative face gasket 302" is disclosed. Face gasket 302" is very similar in all respects to face gasket 302 of FIG. 1, except that there is included an additional layer of felt, or other soft material 313, as shown in FIG. 3, to provide for greater comfort of a user. Also, this softer layer 313 is attached to a thicker posterior surface 307" to accommodate a user with a smaller face in that region. Still further, as shown in FIG. 3, thicker materials at the lower portions 308", 310", 312" of the face gasket 302" may be incorporated as shown so as to accommodate users having smaller facial features in those areas. Also, face gasket 302" comprises a flatter nose bridge portion 310" so as to better accommodate users having that type of facial feature.

This aspect of the invention, comprising easily interchangeable face gaskets 302, 302', 302" using one or more latching mechanisms and alignment guides, addresses the need in the marketplace for an interchangeable face gasket that is relatively inexpensive and easy to manufacture and which may be easily designed to conform to users having different facial characteristics and features such as may be the case for different ethnicities or genders of users. Further, this aspect of the invention provides a structure that may be implemented in conjunction with either a spherical or a cylindrical-type lens member, as well as with lens members having different optical, tinting, heating, single-pane/dual-pane, or other electronic capability characteristics. This, in turn, provides an ability of a military, or other team, to have a stock of outer lens members for general use, if desired, while issuing a custom fit face gasket to each member of the team for personalized and more sanitary use.

Figure 4:
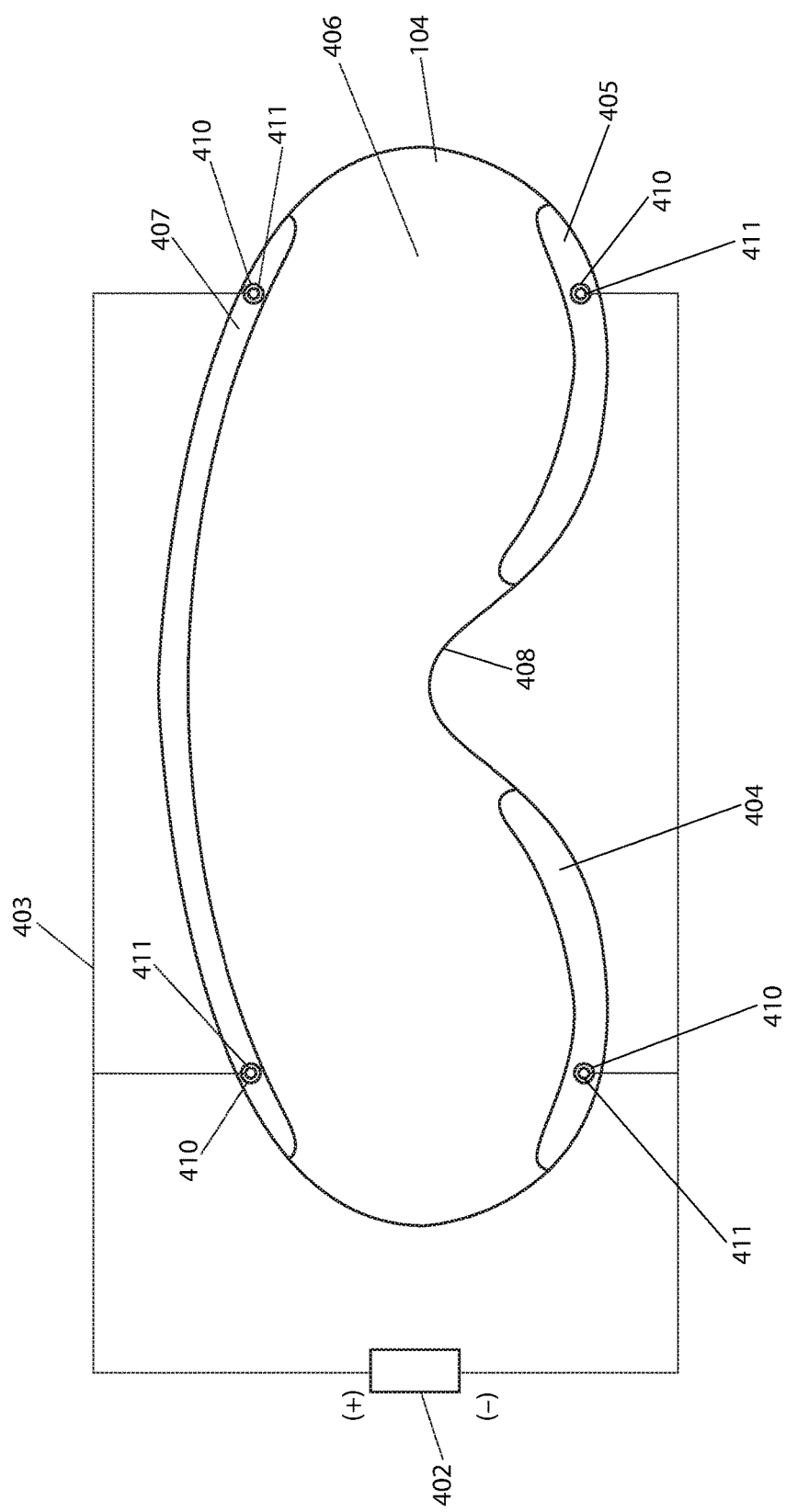
FIG. 4 is an electrical diagram shown together with a bus bar on a thin-film, resistive coating, lens shown in front plan view along with a preferred strategic electrical connection pattern for the goggle of FIG. 1.

Referring now to FIGS. 4 and 5, there is provided the lens member 104 of the goggle with lens and face gasket engagement system 100, the lens member having a resistive heating element 406 deposited thereon, as is known in the art, on an inner surface of the lens member, the resistive heating element being comprised of a thin film heater, resistive wires, or other heating element type such as may be comprised of indium-tin-oxide, carbon nano-wire technology, or other known suitable heating element material.

In FIG. 4, wherein a wiring diagram is shown in connection with a simple lens and bus bar layout, a plurality of bus bars 407, 404, 405 are also shown which may be suitably located as shown and screen printed onto peripheral posterior portions of the resistive heating element 406 which in turn is deposited on the lens member 104. An upper bus bar 407 preferably spans the upper periphery of the lens 104, while two lower bus bars, a lower left bus bar 404 and a lower right bus bar 405, are located on the lowermost peripheral areas of the lens on either side of a nose-bridge area 408 of the lens. The lower bus bars 404, 405 are purposefully split and not located over the bridge of the nose at 408, since to do so would tend to cause a hot spot over the bridge of the nose. Circuit wiring 403 interconnects the bus bars 407, 404, 405 in a resistive circuit to positive and negative terminals, respectively, of a battery 402 that may either be housed on the goggle lens frame, or on, or within, a goggle strap.

Contact points 410, 411 are located at strategic locations on the bus bars 407, 404, 405 to provide substantially even heating of the bus bars and resistive heating element 406. And while there are four contact points and three bus bars shown in the present embodiment, it will be appreciated that other strategic contact points and other distinct bus bars may be employed, depending upon materials used, heating needs, available battery power, and the like, accounting for other design elements of the system, to provide for customized heating, or furthering the goal of even heating, given particular embodiments of the heating system. Such customized heating of a lens heating element and bus bar combination is readily accomplished with the present invention without additional excess labor being required. All a manufacturer needs to do is drop and attach additional contact points into their respective channel members at their appropriate locations for contacting each bus bar according to the design of the overall system.

In the present embodiment, since the upper bus bar 407 is longer across the top of the brow portion of the lens 104, two contact points 410, 412 are made at either end of the bus bar as shown, since otherwise there may be encountered some resistive losses along the length of the bus bar, as would be the case if only one contact point 410, 411 was employed. In this way the novel multi-point contact system as further described easily accommodates the strategic location of the contact point to overcome the otherwise resistive losses to provide even heating from the battery 402 to the upper peripheral bus bar 407 of the system.

Figure 5A:
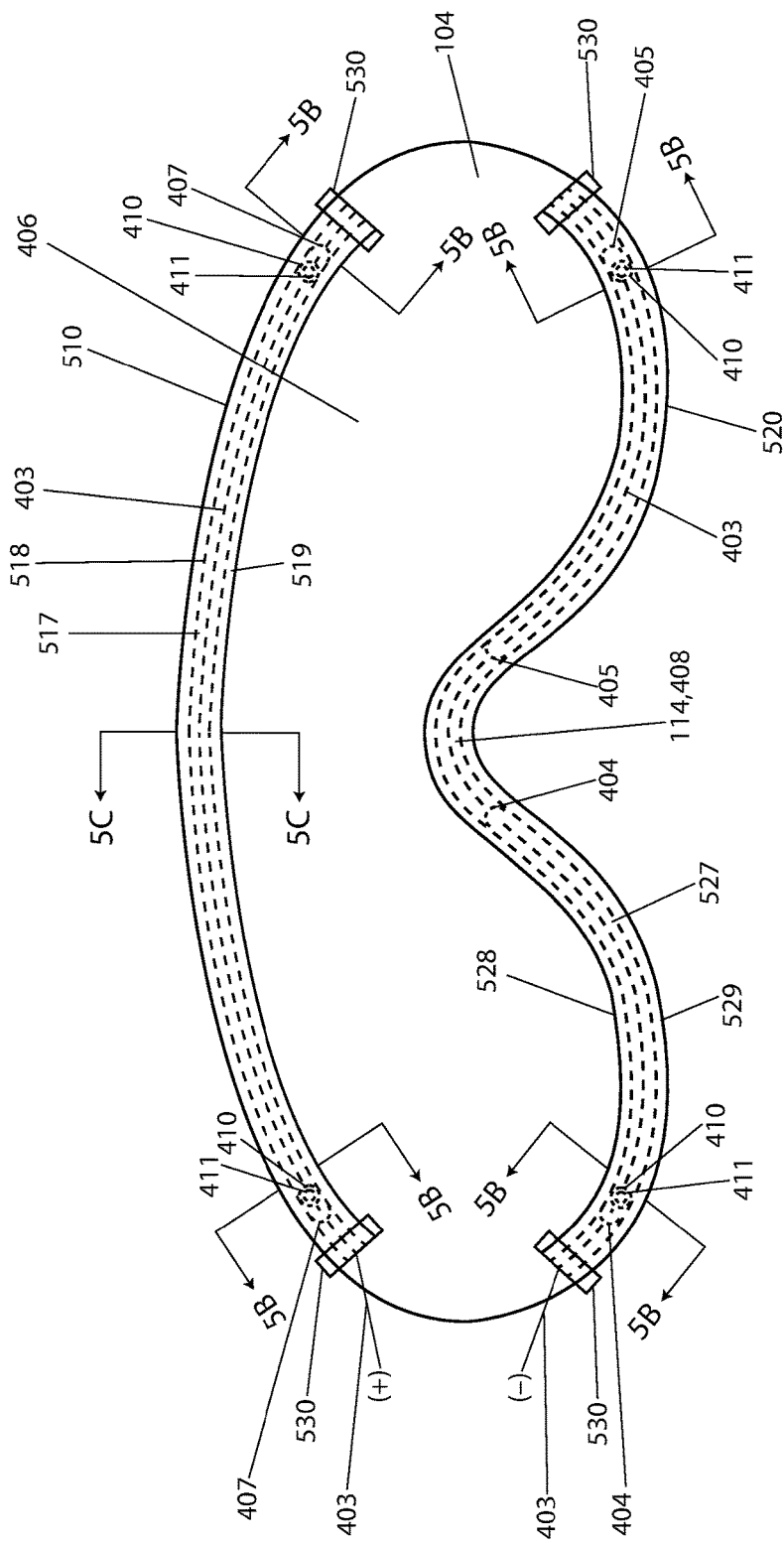
FIG. 5A is a plan view of channel members mounted on the posterior side of a lens (like that shown in FIGS. 1 and 4), positioned over bus bars and on a thin-film, resistive coating and having springy, or compressible, electrically interconnected multi-point contacts within the channel members for engaging and contacting various strategic locations along the bus bars.

The lower left and lower right bus bars 404, 405, respectively, are shorter in length and therefore only require single contact points 410, 411 each to maintain sufficiently even heating of the lens 104. And even though the lower bus bars 404, 405 are split to prevent undue heating over the bridge of the nose at 408, as shown in FIG. 4, a single contact channel 520 is able to be used, as shown in FIG. 5A, to effectively interconnect the bus bars 404, 405 with the battery 402. Nevertheless, and as further described below, if other points of contact for other bus bars were desirable along the path defined by lower bus bars 404, 405, the present system would allow for addition of such contact points along the length without undue additional labor or wiring being required as described above.

In one embodiment of the invention shown in FIGS. 4, 5A and 5B, each contact point on the bus bars 407, 404, 405 preferably comprises a washer 410 having a rivet 411 through the bus bar, the washer, the heating element 406 and the lens substrate 104, thus interconnecting them with the circuit wires 403.

The heating system of this aspect of the invention comprises a plurality of non-conductive plastic "U"-shape (in cross-section) channel members 510, 520 that are mounted on the lens 104 substrate at either end with snaps or clips 530 or other commonly available means for mounting such hardware onto a substrate. Each channel member 510, 520 is mounted over a respective bus bar, or bus bars, 407, 404, 405 face down, with the open portion of the "U" mounted so as to be located directly over and along the length of the bus bar. Channel member 510 is further comprised of a base member 517, and two wall members 518, 519. Similarly, channel member 520 is further comprised of a base member 527 and two wall members 528, 529. Along the length of the base members 517, 527 of each channel member 510, 520 there is located the wiring 403, which may be either a physical wire, or other strip of conductive material. Interposed between, and in contact with, the wiring 403 and each rivet 411 and washer 410 contact, there is provided in the present embodiment, shown in FIG. 5B, a spring contact 513 for creating the contact between the wiring 403 and the bus bars 407, 404, 405 on the heating element 406. Other than at the plurality of strategically located contact points 410, 411, the wiring 403 does not make contact with the bus bars 407, 404, 405 as illustrated at 443 in FIG. 5C.

In an alternative embodiment of the multi-point contact system of the present invention, part of which is shown in FIG. 6, a conductive, spongy, springy, material 411', such as soft conductive foam, may be suitably implemented as well without departing from the scope and spirit of the invention as claimed. Other than the spongy material 411', and the fact that no rivets or washers 410, 411 are needed, this embodiment of this aspect of the invention comprises the same lens substrate 104, heating element 406, channel members 510, 520, bus bars 407, 404, 405, and wiring 403.

It will be appreciated by those skilled in the art that a "U"-shaped channel is not the only way to provide the multi-point system of the invention, but rather any device which provides a sufficient recess to allow the wiring to not contact the bus bar in some places, but allowing a structure to be installed to contact the bus bar at other places, would suffice, such as would an "L"-shaped member, or a semi-circular or otherwise "U"-shaped channel member oriented so as to envelop the anterior and posterior periphery of the substrate, while still holding contacts in place on bus bars on the posterior periphery, may be employed without departing from the true scope of the invention as ultimately claimed.

Preferably, in the case where a battery 402 for heating the goggle with lens and face gasket engagement system 100 resides in, or on, the strap 160 of the system, the wiring 403 of this aspect of the invention interconnecting the multi-point contact points 410, 411 retained within the channel members 510, 520 is partially contained within each channel member and partially contained within the strap.

The channel members 510, 520 of this aspect of the invention may be formed to the contour of the lens member 102 inner (posterior) surface, whether cylindrical, spherical, flat, or otherwise, and the channel members may be adapted for being interconnected with the lens underneath lens frames, or behind a mirrored or dark lens, in order to hide the channel members from external view.

In accordance with this aspect of the invention, the heating element 406 on the lens is preferably releasably interconnected to the power source 402 via wiring 403 and a combination plug member 550, 552, 540. The combination plug member 550, 552, 540 is used at an end 110 of the lens member 102 to interconnect the heating element 406 and the battery 402 via the multi-point contact system described herein. The combination plug member 550, 552, 540 further comprises a female socket 550 (with sockets 552) that are in electrical contact with the heating element 406, and the combination plug member preferably further comprises a male plug 540 at one end of the end of the wiring 403 that is connected with the battery pack 402 as shown carried in a sealed, waterproof container 169 preferably in, or on, the strap 160 of the goggle with lens and face gasket engagement system 100. The wire 403 preferably extends through the strap 160 to the plug member 540 that is able to be easily interconnected with the female socket 550, 552 prior to, or after, engagement of the face gasket 302 with the lens member 102, or alternatively disconnected prior to, or after, disengagement of the face gasket with the lens member. With this embodiment, an on/off switch button 171 (see FIG. 1) is implemented on the battery case 169. However, it will be appreciated that alternately, an on/off button may also be located on the lens frame 102.

Preferably in accordance with this aspect of the invention, the male portion 540 of the plug member has a seal 541 around it that mates with a correspondingly sealed receptacle portion 543 on the female socket 550, 552 to prevent moisture from entering into the electronic system. Likewise, preferably, the electronics of the system are also otherwise sealed to protect against water intrusion into the system.

In accordance with this aspect of the invention, preferably the multi-point contact members 410, 411 are strategically located along an electrical wire, path, or other conductive strip wiring 403 housed at this point within or outside the channel members 510, 520, the contact points being adapted for contacting the bus bars 407, 404, 405 at strategic locations along each bus bar to enable even heating of the lens 102, despite irregular shape and size of the lens and resistive losses along longer bus bar lengths. The bus bars 404, 405 are also broken over the bridge of the nose area 114, 408 of the lens member 102 to aid in preventing a hot spot over the bridge of the nose that would otherwise result. In these ways, consistent and even heating of the lens 102 is aided.

Further, in accordance with this aspect of the invention, preferably the plug 540 and socket 550, 552 members are partially housed within and behind the latch 136 on the side of the lens member 102 where the plug and socket members are located, in order to protect them from being dislodged, bumped, or otherwise damaged during strenuous activity.

Appendix materials comprising renderings of a prototype goggle, or portions thereof, in accordance with the invention are included in Appendix A at the end of this specification.

While a preferred embodiment of the present invention has been shown and described, it will be apparent to those skilled in the art that many changes and modifications may be made without departing from the invention in its broader aspects. For example, it will be appreciated that one of ordinary skill in the art may change the locations of the other protusions to be on either the lens member 102, or the face gasket 302, without departing from the true spirit of this aspect of the invention as claimed. Likewise, it will be apparent that different configurations of multi-point contacts 410, 411, or 411', and corresponding bus bar configurations, may be used to achieve different heating patterns on different shaped and sized lenses. Further, other shaped members may be used to achieve the multi-point contact configurations, and other latch and detent mechanisms may be employed to engage the lens member 102 and the face gasket 302, all without departing from the true scope and spirit of the invention as claimed.

The invention claimed is:

1. A goggle having a lens and interchangeable face gasket engagement system comprising:
   a. a lens member having a posterior inner surface and first and second ends;
   b. latch members pivotably attached to said lens member, one latch member attached adjacent each end of said lens member, each latch member having at least one face gasket member engagement portion;
   c. a flexible face gasket member further comprising a plurality of corresponding latch member engagement portions, each latch member engagement portion of said gasket member for engaging a corresponding one of the gasket member engagement portions of said latch members, at least one of said lens member and said flexible face gasket member further comprising a plurality of other alignment protrusions thereon, whereas the other of said lens member and said flexible face gasket member further comprises corresponding receptacles aligned with the other protrusions for aligning and helping to retain said face gasket member with said lens member when engaged thereon; and
   d. A strap member having first and second ends, each end interconnected to one of said latch members for securing the goggle lens and face gasket engagement system to a user's head.

2. The goggle of claim 1, wherein each said face gasket member engagement portion of each said latch comprises a recessed detent area, wherein each said latch member engagement portion of said face gasket member comprises a supple nub protrusion, each supple nub protrusion for engaging a corresponding recessed detention area of a latch member to thus reinforce retention of said gasket member on said lens member.

3. The goggle of claim 2, further comprising a battery retained on said strap member, said battery retained in a sealed housing having an on/off switch thereon, further comprising a heating element on said lens member, and further comprising upper and lower bus bars interconnecting said heating element and said battery adapted for heating said lens to prevent fogging thereof upon activation by user press of the on/off switch.

4. The goggle of claim 3, wherein each said upper and lower bus bar is painted on peripheral upper and lower portions of said heating element on said lens member, and wherein contact is made between each said bus bar, said heating element and said lens member by means of a contact member on said bus bar further comprising a rivet extending through said contact member, said bus bar, said heating element and said lens member enabling heating said heating element to prevent fogging of said lens member.

5. The goggle of claim 3, wherein each said bus bar is retained in a channel member for interconnecting each said bus bar with said heating element, each channel member also retaining at least one contact member for interconnecting each said bus bar with said battery via circuit wiring for heating said heating element to prevent fogging of said lens member.

6. The goggle of claim 5, further comprising a sealed combination plug, receptacle and wire member for connecting and disconnecting said heating element from said battery.

7. The goggle of claim 6, wherein said sealed combination plug, receptacle and wire member further comprises a female end on one of said channel member and said wire and a male end on the other of said channel member and said wire.

8. A method of installing an interchangeable face gasket on a goggle lens member comprising the steps of:
   a. engaging alignment of face gasket receptacles on lens member alignment protrusions
   b. pivotably operating first and second latches each posteriorly from an open position towards a closed position hinged at corresponding ends of the lens member to initially deform corresponding supple nub protrusions on the face gasket upon initial pivoting engagement of the latches with the face gasket;
   c. continuing to pivotably operate each latch to deform each of the corresponding supple nub protrusions of the face gasket toward continued engagement of each latch with the face gasket; and
   d. finishing pivotable operation of each latch to finally fully engage with each of the latches corresponding supple nub protrusions, each of the supple nub protrusions rebounding into a substantially non-deformation state residing within upper and lower recessed areas of each latch to retain the lens and the face gasket in fully-engaged, but releasable, relationship.

9. A goggle having a lens and interchangeable face gasket engagement system and a multi-point contact electrical contact system adapted for connection with a battery for heating the goggle lens comprising:
   a. a lens member having a posterior inner surface and first and second ends;
   b. latch members pivotably attached to said lens member, one latch member attached adjacent each end of said lens member, each latch member having at least one recessed detent area;
   c. a flexible face gasket member further comprising a plurality of corresponding supple nub protrusions, each supple nub protrusion for residing in a corresponding one of the recessed detent areas of said latch members, at least one of said lens member and said flexible face gasket member further comprising a plurality of other alignment protrusions thereon, whereas the other of said lens member and said flexible face gasket member further comprises corresponding receptacles aligned with the other protrusions for aligning and helping to retain said face gasket member with said lens member when engaged thereon;
   d. a strap member having first and second ends, each end interconnected to one of said latch members for securing the goggle to a user's head;
   e. a battery retained on said strap member, said battery retained in a sealed housing having an on/off switch thereon;
   f. a resistive heating element deposited on a posterior surface of said lens member;
   g. upper and lower bus bars for contacting said heating element on said lens member;
   h. upper and lower "U"-shaped cross-section non-conductive channel members attached with an open end of each "U" of each said channel member positioned over each said bus bar;
   i. a plurality of strategically-located and compressible contact points, the contact points adapted for interconnecting said heating element and said battery via wiring contained partially within said channel members and in a way that said wiring does not contact any said bus bar except at said contact locations within said channel members, said battery thus being adapted for heating said heating element on said lens member upon activation by a user pressing said on/off button.

10. The goggle of claim 9, further comprising a sealed combination plug, receptacle and wire member for connecting and disconnecting said heating element from said battery.

11. The goggle of claim 10, wherein said sealed combination plug, receptacle and wire member further comprises a female end on one of said channel member and said wire and a male end on the other of said channel member and said wire.

\* \* \* \* \*